United States Patent [19]

Tsuge et al.

[11] Patent Number: 5,062,798
[45] Date of Patent: Nov. 5, 1991

[54] SIC BASED ARTIFICIAL DENTAL IMPLANT

[75] Inventors: Kazuto Tsuge; Masateru Hattori; Kazuo Kondo; Yoshimasa Shibata, all of Aichi, Japan

[73] Assignee: NGK Spark Plug Co., Ltd., Aichi, Japan

[21] Appl. No.: 343,207

[22] Filed: Apr. 26, 1989

[30] Foreign Application Priority Data

Apr. 27, 1988 [JP] Japan .................. 63-102797
May 18, 1988 [JP] Japan .................. 63-119269

[51] Int. Cl.$^5$ ............................................. A61C 8/00
[52] U.S. Cl. ..................................... 433/201.1; 433/173
[58] Field of Search ........................... 433/201.1, 173

[56] References Cited

U.S. PATENT DOCUMENTS

| | | | |
|---|---|---|---|
| 3,707,006 | 12/1972 | Bokros et al. | 433/201.1 |
| 4,446,579 | 5/1984 | Inamori et al. | 433/173 |
| 4,483,678 | 11/1984 | Nishio et al. | 433/201.1 |
| 4,497,629 | 2/1985 | Ogino et al. | 433/201.1 |
| 4,604,059 | 8/1986 | Klaus et al. | 433/201.1 |
| 4,806,383 | 2/1989 | Poltz | 433/201.1 |

FOREIGN PATENT DOCUMENTS 0249632  9/1987  Fed. Rep. of Germany ... 433/201.1

Primary Examiner—John J. Wilson
Attorney, Agent, or Firm—Finnegan, Henderson, Farabow, Garrett and Dunner

[57] ABSTRACT

An artificial radix dentis comprises a prong portion buried in an alveolar bone, which is made of a SiC-based ceramic material or is covered with a SiC-based film.

7 Claims, 2 Drawing Sheets

SIC BASED ARTIFICIAL DENTAL IMPLANT

BACKGROUND OF THE INVENTION

The present invention relates to an implant, more particularly, to a dental implant or an artificial radix dentis (root of a tooth) that is to be buried in the natural gums and alveolar bone.

While the artificial root of a tooth is required to possess various characteristics, the most important are the following three:

1) it does not do any harm to the body by releasing ions or some other deleterious substances (i.e., it has biochemical safety); 2) it has good affinity for body tissues including bone (i.e., it has biocomptability); and 3) it maintains balance in strength with other body tissues (i.e., it has mechanical balance).

Dental implant materials known today include ceramics based on apatite $[Ca_5(PO_4)_3.(OH,F,Cl)]$, metals, alumina or zirconia, which are used on their own, and substrates such as metals, alumina or zirconia, which are coated with a calcium phosphate type film. Metals conventionally used as dental implant materials include titanium, cobalt, chromium, tungsten and molybdenum alloys. Alumina used as a dental implant material has been in the form of a single crystal, a combination of single-crystal and polycrystalline structures, and a combination of single-crystal, porous and polycrystalline structures. These and other prior art techniques are described in many patents including JP-A-55-140756 (the term "JPA" as used herein means "an unexamined published Japanese patent application"), JP-A-59-11843 and JP-A-59-82849. JP-A 55-140756 describes a calcium phosphate type sinter, and JP-A-59-11843 and JP-A-59-82849 describe dental implants that are composed of stainless steel and other substrates that are coated with a calcium phosphate type film.

These conventional dental implants, however, have had the following defects. Metals exhibit satisfactory mechanical strength but being foreign to bones, they are not highly biocompatible. In addition, some metals are ionized and will dissolve out to do harm to body tissues. Thus, it is not preferable to use metals alone in an uncovered state. Alumina and zirconia will do no harm to body tissues even if they are used on their own. However, they are too hard compared to natural bone and are not highly compatible with the latter. Thus, during prolonged use, gaps will form between the implant and an adjacent bone, thereby injuring the maxilla or mandible in the joined area. In addition, alumina and zirconia involve cumbersome procedures in handling artificial radix dentis since they cannot be fitted into the maxilla or mandible without being supported by bridges. Metal, alumina or zirconia substrates coated with a calcium phosphate type film have the problem of insufficient adhesion between the substrate and the coating. A problem with apatite-based ceramics is that they must have a considerable thickness in order to maintain a satisfactory level of strength for practical purposes. Furthermore, the bite, or the pressure developed in closing the jaws, will be transmitted directly to the alveolar bone, imparting unpleasant feeling to the user. Thus the artificial radix dentis made of ceramics is not completely satisfactory, especially in terms of biocompatibility and mechanical balance.

SUMMARY OF THE INVENTION

An object, therefore, of the present invention is to provide an artificial radix dentis(dental implant that has improved biochemical safety, biocompatibility and mechanical balance and which can be used as effectively as natural radix dentis without imparting any unplesant feeling to the user.

This object of the present invention can be attained by an articial radix dentis or a dental implant which is characterized in that the prong, or the part corresponding to the root of a tooth to be buried in bone, is made of SiC-based ceramics or is covered with a SiC-based film. The SiC-based film is preferably formed by a chemical vapor-phase deposition (CVD) process.

The dental implant of the present invention is intended to assist in the mounting of denture, or an artificial tooth, and consists of three distinct parts, the prong which is to be buried in the maxilla or mandible when the denture is fitted into either jaw bone, the part which is to be buried in the gingival mucosa which covers the jaw bone, and the denture mounting part which protrudes through the gingival mucosa to become exposed in the oral cavity.

The dental implant of the present invention is characterized in that the prong which is to be buried in bone is made of SiC-based ceramics or is covered with a SiC-based film which precludes the possibility of the prong of doing harm to body tissues. In addition, the prong is believed to be as compatible as natural radix dentis with bone, so that when this dental implant is fitted into an alveolus dentalis (tooth socket), it is anticipated that a periodontal membrane comparable to the natural one will be formed as effectively as in the case of natural teeth.

A natural tooth is fitted in an alveolus dentalis, or a cavity in the maxilla or mandible, and attached by means of the periodontal membrane which serves as a kind of cushion during mastication. Natural periodontal membrane has bundles of Sharpey's fibers which extend in a direction substantially perpendicular to the surfaces of radix dentis and the wall of the tooth pocket. An experiment with animals showed that bundles of collagenous fibers extending in a direction perpendicular to the surface of radix dentis formed when the dental implant of the present invention was fitted into bone. It is therefore anticipated that a membrane similar to the human periodontal membrane would also form when this dental implant is fitted into the maxilla or mandible; thus, this dental implant could most probably be used for a prolonged period without damaging the maxilla or mandible to which it is attached and without imparting unpleasant feeling to the user.

The thickness of the SiC-based film needs to be sufficient to allow for the formation of a membrane that is similar to the natural periodontal membrane when the dental implant of the present invention is fitted into bone, and it may have a thickness of at least 0.1 $\mu$m, preferably between 1 and 10 $\mu$m.

The SiC-based film preferably contains at least 95 wt% of SiC.

The SiC-based film will adhere firmly to the substrate of the prong which is covered with this film and no ionization will occur even if said substrate is made of a metal. The SiC-based film may have a smooth surface but for the purpose of forming a periodontal membrane, the surface of this film is preferably porous rather than smooth.

The preferred crystallographic structure of SiC in the SiC-based film is of the β-type.

When the SiC-based film is to be formed by the reaction of chemical vapor-phase deposition, the starting gas is preferably selected from among $CH_3SiCl_3$, $(CH_3)_2SiCl_2$, $Si(CH_3)_4$, etc. and the reaction temperature may be selected from the range of 900–2,000° C., typically in the neighborhood of 1,400° C.

The prong which is to be covered with the SiC-based film should be so configured as to ensure strong attachment to the maxilla or mandible, preferably to provide a wider area of contact with either jaw bone. To this end, the prong may be threaded, provided with longitudinal or transverse grooves, corrugated or rendered porous. A threaded prong offers the advantage that the dental implant can be securely fixed immediately after it is fitted into bone.

The substrate of the prong which is to be covered with the SiC-based film may be formed of a material that adheres strongly to said film and that imparts satisfactory mechanical strength to the dental implant. Preferred examples of such materials include stainless steels such as nickel-chrome alloys, high-strength metals such as titanium and titanium alloys, high-melting point metals such as tungsten and molybdenum, and high-strength ceramics such as alumina, zirconia, spinel, Sialon and silicon nitride. Since the prong is covered with the SiC-based film, the substrate of the prong may be made of a metal without suffering from the disadvantage of ionization of the metal.

The two other parts of the dental implant of the present invention, namely, the part to be buried in the gingival mucosa and the denture mounting part which protrudes into the oral cavity, may be made of a material which is the same as that of the substrate of the prong and which is continuous from the latter to make up a unitary assembly. However, in order to insure greater strength, these two parts may be formed of a crystallographic structure or material that differs from any one of those above in connection with the substrate of the prong, and the three parts are combined to make a unitary assembly.

In order to provide a higher degree of biocompatibility and to ensure stronger adhesion to denture, each of the part that is to contact the gingival mucosa and the denture mounting part which is to protrude into the oral cavity may preferably be coated with a suitable film. For example, the part that is to contact the gingival mucosa may be covered with a calcium phosphate type ceramic film and this film will provide better affinity for the gingival mucosa through decomposition and other reactions that occur at the interface of contact with said gingival mucosa. If a metal is to be used as the constituent material of the part that is to be buried in the gingival mucosa, it should be covered with a film that is at least capable of preventing ionization of said metal.

In order to insure satisfactory adhesion between these covering films and the substrate of the part that is to be buried in the gingival mucosa or of the denture mounting part, both of which parts are to be covered with these films, an appropriate film or layer that have good adhesion to these covering films and substrates may be provided between these two components.

DETAILED DESCRIPTION OF THE INVENTION

Figures 1A, 1B:
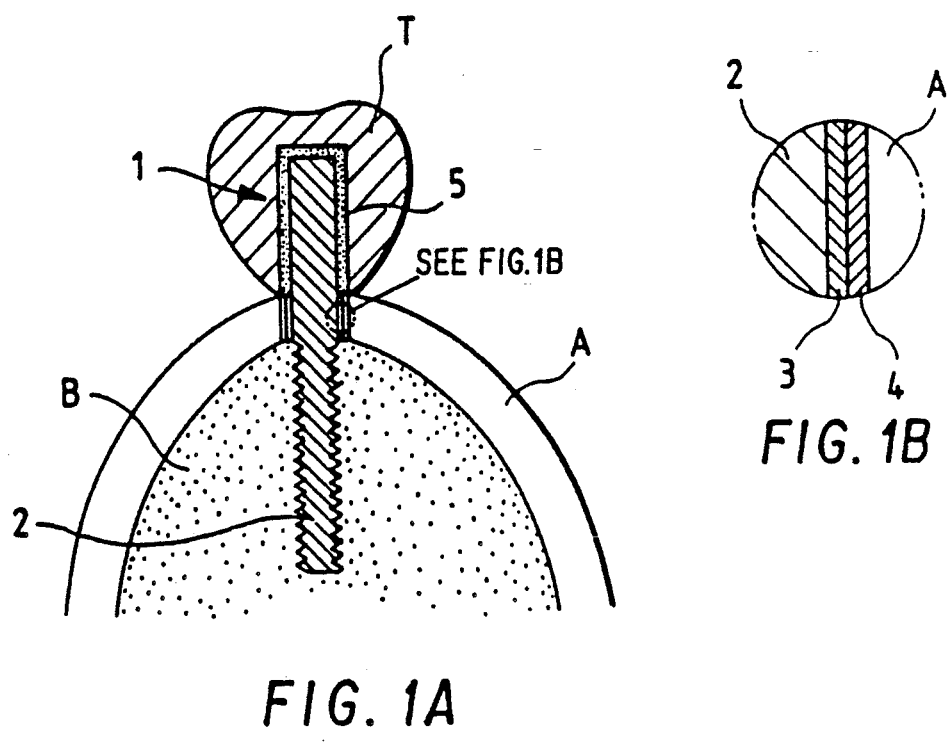
FIG. 1 is a cross sectional view showing an example of the artificial radix dentis of the present invention which is fitted into bone, with the inset showing part of this radix dentis at an enlarged scale.

The artificial radix dentis of the present invention must be such that the part thereof which is to be buried in the alveolar bone is made of a SiC based ceramic material (which is hereinafter sometimes referred to as "a SiC ceramic material"). This is in order to ensure that after the radix dentis is fitted into bone, a fibrous tissue that extends in a direction perpendicular to the surfaces of both the radix dentis and the alveolar bone, namely, a tissue having the same function as that of the natural periodontal membrane (which is hereinafter referred to as the "artificial periodontal membrane"), will be developed between the radix dentis and the alveolar bone, thereby imparting cushioning properties during mastication. Said requirement should also be met in order to maintain a sufficient level of strength to withstand practical applications and to produce artificial radix dentis in a compact form. The part which is to be buried in the alveolar bone, generally corresponds to that site of natural radix dentis where the periodontal membrane forms. The SiC based ceramic material preferably contains SiC in an amount of at least 90%, more preferably at least 95%, of the total weight of the ceramic material. Desired artificial periodontal membrane may not be formed if the SiC content is less than 90% of the SiC ceramic material. The remainder of the SiC ceramic material may be occupied by a firing aid selected from among elemental nonmetals and metals such as B, C, Al, Fe and W, boron compounds such as $B_4C$, BN and BP, aluminum compounds such as AlN, $Al_4C_3$ and $AlB_2$, and other materials. The SiC ceramic material preferably has an average crystal grain size of 1–5 μm and a relative density which is 90–100% of the theoretical one (porosity of 10–0%). These conditions should preferably be satisfied in order to provide satisfactory biocompatibility and mechanical balance for the artificial radix dentis of the present invention.

The SiC in the SiC ceramic material may be either α-SiC or β-SiC. The SiC ceramic material may only be present on the surface of the artificial radix dentis since it is capable of forming an artificial periodontal membrane. The surface layer formed of the SiC ceramic material may have a thickness of at least 5 μm. The substrate of the artificial radix dentis may be formed of a high-strength material such as a metal (e.g. steel, titanium or titanium alloys), alumina, zirconia, spinel, Sialon or silicon carbide.

The SiC ceramic material in the area of contact with the gingiva must be covered with a predetermined first layer, which in turn must be covered with a predetermined second layer.

The first layer is positioned intermediate between the SiC ceramic material (the base material) and the second layer so as to improve the adhesion between these two parts. The first layer is preferably made of a phosphate glass represented by the formula $P_2O_5$-MO (MO denotes an oxide of an alkali metal or an alkaline earth metal or at least one metal oxide selected from among ZnO, $Al_2O_3$, $SiO_2$, etc.). The content of $P_2O_5$ as the principal component is at least 40 mol% and particularly preferred examples of the system of the first layer are $P_2O_5$-BaO-CaO, $P_2O_5$-CaO-ZnO, and $P_2O_5$-BaO-MgO-$Al_2O_3$. A specific example is composed of 40–75 mol% of $P_2O_5$ and 20–55 mol% of at least one component selected from the group consisting of BaO, CaO, MgO, ZnO, $Na_2O$ and $K_2O$ (see JP-A-55-140756).

The phosphate glass of which the first layer is made may be crystallized glass. Advantageously, a lowexpansion material may be added to calcium phosphate glass so as to adjust its thermal expansion coefficient to lie within the range of $30$–$60 \times 10^{-7}$/° C. This is in order to attain thermal expansion match between the first layer and the SiC ceramic material so as to ensure that the strength of bonding between the two parts will not decrease during use. The thickness of the first layer is preferably adjusted to be within the range of 0.5–10 $\mu$m. If the thickness of the first layer is less than 0.5 $\mu$m, the desired adhesion is not attainable. If the thickness of the first layer exceeds 10 $\mu$m, the characteristics of the SiC ceramic material and the material of the second layer may not be exploited to the fullest extent.

The second layer serves to provide improved biocompatibility, or better affinity for the gingiva, by initiating decomposition or other reactions at the interface of contact with the gingiva. The second layer is preferably made of a calcium phosphate type ceramic material, which includes ceramics formed of apatite and calcium phosphate. Apatite is the collective name for compound represented by the formula ($Ca_5(PO_4)_3$·(OH,F,Cl)), and calcium phosphate is the collective name for compounds in which CaO and $P_2O_5$ are present in various proportions. The atomic ratio of Ca to P in the apatite or calcium phosphate may be selected from the range of 1.4–1.75. The calcium phosphate type ceramics may contain various firing accelerators in addition to the apatite or calcium phosphate as the principal component. Illustrative firing accelerators are: calcium phosphate glass having a Ca/P atomic ratio of 0.2–0.75 which is contained in an amount of 0.5–15 wt% (see JP-A-55-56062); $P_2O_5$-MO glass of the type described above which is contained in an amount of 0.5 –15 wt%; and combinations of these glasses with $Y_2O_3$ which is contained in an amount of 3–23 wt% (see JP-A-55-140756 and JP-A-55-80771). The second layer preferably has a thickness of at least 10 $\mu$m in order to attain desired biocompatibility. The second layer preferably has an average crystal grain size of no more than 3 $\mu$m and a relative density which is at least 50% of the theoretical one. These conditions should preferably be satisfied in order to provide satisfactory biocompatibility and mechanical balance for the artificial radix dentis of the present invention.

The surface of the artificial radix dentis of the present invention, namely, the surface of the SiC ceramic material or the second layer. preferably has asperities at sites corresponding to living periodontal tissues, particularly at sites where the radix dentis is buried in the alveolar bone. This is in order to maintain strong adhesion between the artificial radix dentis and the surrounding periodontal tissues. Asperities may be provided by various means including forming spiral or linear grooves or rendering the surface of the radix dentis porous. From the viewpoint of manufacturing process, all part of the artificial radix dentis except the first and second covering layers is advantageously made of the SiC ceramic material alone. It should, however, be noted that the part of the radix dentis other than the area corresponding to the alveolar bone need not necessarily be formed of the SiC ceramic material since there is no need to form an artificial periodontal membrane in that part. If desired, the already-mentioned high-strength material (i.e., metals and ceramics) may be employed in that part.

The process for producing the artificial radix dentis of the present invention will be described hereinafter. The SiC ceramic material can be sintered by hot press sintering, normal sintering, reactive sintering, recrystallization or chemical vapor-phase deposition. If a hot press sintering method is to be adopted, the preferred starting material is the powder of $\beta$-SiC having a purity of at least 95% and an average particle size of no more than 1.5 $\mu$m. This powder may be sintered in an inert atmosphere at a temperature of 1,500–2,100° C. and at a pressure of 300–600 atm. In hot press sintering, Fe, Al, $Al_2O_3$, W, B or C may be added as a sintering aid. If a normal sintering method is to be adopted, a starting powder containing B, C, and optionally $B_4C$, BN, BP, Al, AlN, $Al_4C_3$, $AlB_2$, etc. as a sintering aid may be sintered in an inert gas or under vacuum at a temperature of about 2,000° C. In reactive sintering, a compact of the mixed powder of $\alpha$-SiC and C may be impregnated with molten Si to form $\beta$-SiC by reaction, which is then sintered in a vacuum atmosphere at 1,600–1,700° C. In order to form pores, a that will burn away such as a carbon powder (20 –500 $\mu$m) or an organic matter may be mixed in a slurry of calcium phosphate.

The SiC ceramic material may be covered with the first and second layers by brush-coating, dip-coating, spray-coating or otherwise coating the SiC ceramic material with a solution or powder of the necessary material, and thereafter firing the applied coating. The first and second layers may also be formed by customary vapor-phase deposition techniques such as sputtering, evaporation and thermal spraying. The SiC ceramic material may be fired either separately or simultaneously with the first and second layers.

When used, the artificial radix dentis of the present invention is buried in the alveolar bone, with its open end covered with an artificial crown which is generally equivalent to natural enamel. The radix dentis may be buried (or implanted) by the following procedures: the living gingival mucosa is cut away; a threaded hole that conforms to the shape of the radix dentis is drilled in the maxilla or mandible; and the radix dentis is threaded into the hole. The tip of the implanted radix dentis is capped with an artificial crown that is attached by means of an adhesive.

An example of the artificial radix dentis of the present invention as buried in the alveolar bone is shown in FIG. 1 in which the radix dentis is indicated by numeral 1. The other numerals and symbols used in FIG. 1 refer to the following: 2, the SiC ceramic substrate; 3, the first layer made of phosphate glass; 4, the second layer made of a calcium phosphate type ceramic material; 5, adhesive; A, gingiva; B, alveolar bone; and T, artificial crown.

EXAMPLE 1

Mixtures consisting of 98 wt% of a 99% pure $\beta$-SiC powder ($\beta$ proportion, 99%; average particle size, 0.5 $\mu$m) and 2 wt% of a 99% pure $Al_2O_3$ powder (average particle size, 0.5 $\mu$m) were press formed into disks having a diameter of 10 mm and a thickness of 1 mm (these disks were to be used as specimens in Test 1) and cylinders (3 mm$\phi \times$9 mm) for use as specimens in Test 2. These compacts were hot pressed in an argon atmosphere at 1,800 -2,075° C. and at 500 atm to prepare SiC sinters.

The biochemical safety, biocompatibility and mechanical balance of these SiC sinters were investigated by the following methods. Similar tests were conducted on comparative specimens which were commercial grades of $ZrO_2$ sinter (product of NGK Spark Plug Co., Ltd.) and glass (product of Ikemoto Co., Ltd.) having the same dimensions as noted above.

TEST 1 (ON BIOCHEMICAL SAFETY)

Materials and method

L-cell line (fibroblasts of C3H mouse) was treated with 0.05% (wt%) trypsin and suspended loosely in an Eagle's MEM culture solution (Product of Nissui Seiyaku Co., Ltd.) supplemented with 2 mM L-glutamine and 10% (wt%) calf serum. A five hundred cells as counted with a hemocytometer were put into plastic Petri dishes together with 10 ml of a normal culture solution and cultured at 37° C. for 2 hours in a mixed gas atmosphere (5% $CO_2$ and 95% air).

The individual specimens (SiC, $ZrO_2$ and glass) were put into the Petri dishes and cultured for 2 weeks. Thereafter, the cultures were fixed with methanol and stained with a Giemsa solution. The number of colonies each consisting of no less than 50 cells was counted under a stereoscopic microscope.

Results

The results are shown in the following table 1.

TABLE 1

| Specimen | Colony Average number | Percentage of colony formation |
|---|---|---|
| SiC | 336.3 | 67.3 |
| $ZrO_2$ | 298.7 | 59.7 |
| Glass | 338.5 | 67.7 |

The above data establishes the fact that the SiC ceramic material has no cytotoxicity.

TEST 2 (ON BIOCOMPATIBILITY)

Materials and method

Two holes 3 mm in diameter that reached the medullary space were drilled in each of the thighs of a mature rabbit (Japanese white type, male, 3 kg in body weight) at a position about 10 mm distant from the proximal metaphysis. A SiC specimen was buried in each of the holes in the right thigh, whereas a $ZrO_2$ specimen was put into each of the holes in the left thigh. The peristeum and skin were thereafter sutured. After a certain period of time, the femoral bones of the rabbit were dissected frozen and the tissue specimens were decalcified with 0.5 M EDTA, sliced and post-fixed. After dehydration, the specimens were embedded in an epoxy resin and sliced to very thin (0.1 $\mu$m) sections, which were double-stained and examined under a scanning and a transmitting electron microscope.

Results (1) The observation under a scanning electron microscope showed that both the SiC and $ZrO_2$ specimens were covered with fibrous tissues that matured with time. This indicated the absence of direct bonding between the specimens and the bone tissue.

Figure 2A:
FIG. 2A is a transmitting electron micrograph that shows the shape of fibers present between a comparative $ZrO_2$ sample and bone.
Figure 2B:
FIG. 2B is a micrograph showing at an enlarged scale that part of the fibers which runs parallel to the surface of radix dentis.
Figure 2C:
FIG. 2C is a transmitting electron micrograph that shows the shape of fibers present between a SiC sample as an example of the present invention and bone.
Figure 2D:
FIG. 2D is a micrograph showing at an enlarged scale that part of the fibers which runs in a direction perpendicular to the surface of radix dentis.

(2) The results of the observation under a transmitting electron microscope are shown in FIGS. 2A to 2D. In each micrograph, the buried SiC or $ZrO_2$ specimen is indicated by the vertical bar(I), and the horizontal bar(—) at the lower left position refers to the length of 1 $\mu$m. As FIGS. 2C and 2D show, fibrous tissues that ran in a direction perpendicular to the surface of the SiC specimen (as indicated by arrows) formed 3 weeks after the implantation. FIG. 2D is a partial enlarged view of the so formed fibrous tissues. As FIGS. 2A and 2B show, fibrous tissues that ran parallel to the surface of the $ZrO_2$ specimen (as indicated by arrows) formed between the specimen and the surrounding bone tissue. FIG. 2B is a partial enlarged view of the so formed fibrous tissues.

One will, therefore, understand that when the SiC specimen is used as an artificial radix dentis, fibrous tissues similar to those of the natural periodontal membrane will grow to exhibit good cushioning properties during use. In other words, the SiC specimen has satisfactory biocompatibility.

TEST 3 (ON MECHANICAL BALANCE)

The flexural strength and Young's modulus of the SiC sinters were higher than those of natural radix dentis (about 2 kgf/mm$^2$ in dentin) and were approximately 50 kgf/mm$^2$ and $4 \times 10^6$ kgf/cm$^2$, respectively.

It is therefore clear that the SiC ceramic material of the present invention is also improved in terms of mechanical balance. Thus, unlike the conventional apatite type ceramics, this SiC ceramic material can be used satisfactorily as an artificial radix dentis without causing any problem.

EXAMPLE 2

The SiC ceramic material prepared in Example 1 was shaped into a cylinder having a diameter of 2.5 mm and a length of 25 mm and helical grooves were cut at a pitch of 1 mm in the surface of the cylinder. The thus threaded cylinder was used as a base material.

(1) Twenty kilograms of $CaCO_3$ was mixed with 44 kg of $H_3PO_4$ (89%) and the resulting mixture was fired at 1,300° C. for 2 hours. The atomic Ca/P ratio in the fired product was about 0.5. The fired product was ground into a powder so that the particles of 5 $\mu$m or greater in size would be 40% on trommel. The powder was put into a 1% aqueous solution of methyl cellulose and stirred to form a calcium phosphate slurry. The previously prepared base material was immersed in the slurry and thereafter dried and fired in air atmosphere at 700° C. to have the surface of the base material covered with the first layer of calcium phosphate.

(2) In the next step, a commercial grade of hydroxyapatite having an average particle size of 0.1 $\mu$m was calcined at 800–1,100° C. The calcined hydroxyapatite was ground into a powder having an average particle size of 3–4 $\mu$m and the particles were suspended in alcohol. The base material covered with the first layer of calcium phosphate in step (1) was brush- or dipcoated with this suspension, dried and fired in air atmosphere at 800–1,200° C. for 45 minutes to have the surface of the first layer covered with the second layer of hydroxyapatite.

The thus prepared artificial radix dentis had the same characteristics as those of the sample prepared in Example 1 and it also exhibited better biocompatibility at the area where it would contact directly with the gingiva.

EXAMPLE 3

A tungsten cylinder having a diameter of 2.5 mm and a length of 25 mm was threaded at a pitch of 1 mm in the area extending over a distance of 15 mm from one end. A SiC film 10 μm thick was deposited by CVD reaction over the entire surface of the cylinder. The CVD reaction was performed at about 1,400° C. using $CH_3SiCl_3$ (C/Si=1) as a feed gas.

EXAMPLE 4

A molybdenum cylinder having a diameter of 2.5 mm and a length of 25 mm was prepared and a SiC film 8 μm thick was deposited by CVD reaction over the entire surface of the cylinder. The CVD reaction was performed as in Example 3.

EXAMPLE 5

An alumina ceramic cylinder having a diameter of 2.5 mm and a length of 25 mm was prepared and a SiC film 10 μm thick was deposited by CVD reaction over the entire surface of the cylinder. The CVD reaction was performed as in Example 3.

EXAMPLE 6

A zirconia ceramic cylinder having a diameter of 2.5 mm and a length of 25 mm was prepared and a SiC film 10 μm thick was deposited by CVD reaction over the entire surface of the cylinder. The CVD reaction was performed as in Example 3.

COMPARATIVE EXAMPLE 3

Zirconia ceramic cylinder having a diameter of 2.5 mm and a length of 25 mm.

EXPERIMENT 1

Holes 3 mm in diameter that reached the medullary space were drilled in each of the thighs of a mature rabbit (Japanese white type, male, 3 kg in body weight) at a position about 10 mm distant from the proximal The dental implants prepared in Examples 3–6 and Comparative Example 3 were buried in the holes. The peristeum and skin were thereafter sutured. Three weeks after the implantation, the femoral bones of the rabbit were dissected frozen and the tissue specimens were decalcified with 0.5 M EDTA, sliced and postfixed. After dehydration, the specimens were embedded in an epoxy resin and sliced to very thin (0.1 μm) sections, which were double-stained and examined under a scanning and a transmitting electron microscope.

RESULTS (1) The observation under a scanning electron microscope showed that all the dental implants were covered with fibrous tissues that matured with time. This indicates the absence of direct bonding between the dental implants and the bone tissue.

(2) The results of the observation under a transmitting electron microscope showed that a number of fibrous tissues 21 that ran in a direction generally perpendicular to the surface of SiC film 20 has formed between each of the dental implants prepared in Examples 3–6 and the surrounding bone tissue (see FIGS. 2C and 2D). As for the dental implant prepared in Comparative Example 3, fibrous tissues 31 that ran parallel to the surface of the implant 30 had formed (see FIGS. 2A and 2B). It is therefore anticipated that when the dental implants prepared in Examples 3–6 are fitted into the maxilla or mandible, a periodontal membrane will also form that has bundles of fibers extending in a direction substantially perpendicular to the surfaces of both the radix dentis and the tooth socket. This possibility is supported by FIGS. 2C and 2D.

EXPERIMENT 2

L-cell line (fibroblasts of C3H mouse) was treated with 0.05% (wt%) trypsin and suspended loosely in an Eagle's MEM culture solution (Product of Nissui Seiyaku Co., Ltd.) supplemented with 2 mM L glutamine and 10% of the total weight of calf serum. A five hundred cells as counted with a hemocytometer were put into three plastic Petri dishes together with 10 ml of a normal culture solution and cultured at 37° C. for 2 hours in a mixed gas atmosphere (5% $CO_2$ and 95% air). Then, disks (10 mm diameter ×1 mm thickness) of SiC, $ZrO_2$ and a glass plate (control) were put into the Petri dishes, one disk per dish, and cultured for 2 more weeks. Thereafter, the cultures were fixed with methanol and stained with a Giemsa solution. The number of colonies each consisting of no less than 50 cells was counted under a stereoscopic microscope.

RESULTS

The results are shown in the following table 2.

TABLE 2

| | Colony | |
|---|---|---|
| Specimen | Average number | Percentage of colony formation |
| SiC | 336.3 | 67.3 |
| $ZrO_2$ | 298.7 | 59.7 |
| Glass | 338.5 | 67.7 |

The above data establishes the fact that the SiC has no cytotoxicity.

The artificial radix dentis or the denture mounting dental implant of the present invention has several advantages that can be summarized as follows:

(1) The prong portion of the implant which is to be buried in bone will do no harm to body tissues since it is covered with a film that is chiefly composed of SiC having no cytotoxicity.

(2) The affinity of the prong portion for bone is considered to be comparable to that of natural radix dentis, so that when the implant is fitted into the maxilla or mandible, a periodontal membrane similar to the natural one is expected to form. As a result, the implant can be used for a prolonged period without damaging the maxilla or mandible and without causing any unpleasant feeling to the user.

(3) The SiC-based film has good adhesion to the substrate of the prong which is to be covered with said film. If the substrate of the prong is made of a high strenght metal or ceramic material, the implant can be provided with a sufficient level of strength to withstand practical use.

What is claimed is:

1. An artificial radix dentis comprising a first portion adapted to be buried in an alveolar bone and a second portion adapted to contact a gingiva, wherein at least an outermost layer of said first portion consists essentially of a SiC-based ceramic material.

2. An artificial radix dentis according to claim 1, wherein said second portion is covered with a first layer made of a phosphate glass, and wherein said first layer is covered with a second layer made of a calcium phosphate type ceramic material.

3. An artificial radix dentis according to claim 1, wherein said SiC-based ceramic material contains SiC in an amount of at least 90% of the total weight of said ceramic material.

4. An artificial radix dentis according to claim 1, wherein said SiC-based ceramic material has an average crystal grain size of 1-5μm and a porosity of 0-10%.

5. An artificial radix dentis comprising a prong portion adapted to be buried in a bone, wherein said prong is covered with a film consisting essentially of SiC.

6. An artificial radix dentis according to claim 5, wherein said SiC-based film is formed by a chemical vaporphase deposition process.

7. The artificial radix dentis of claim 5, wherein said film is at least 95% by weight SiC.

* * * * *